(12) United States Patent
Aoki (10) Patent No.: US 11,366,130 B2
(45) Date of Patent: Jun. 21, 2022

(54) DETECTION DEVICE AND DETECTION METHOD

(71) Applicant: OTSUKA PHARMACEUTICAL CO., LTD., Tokyo (JP)

(72) Inventor: Youichi Aoki, Saitama (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 331 days.

(21) Appl. No.: 15/742,777

(22) PCT Filed: Jul. 6, 2016

(86) PCT No.: PCT/JP2016/070047
§ 371 (c)(1),
(2) Date: Jan. 8, 2018

(87) PCT Pub. No.: WO2017/006969
PCT Pub. Date: Jan. 12, 2017

(65) Prior Publication Data
US 2018/0196077 A1     Jul. 12, 2018

(30) Foreign Application Priority Data
Jul. 7, 2015   (JP) .............................. JP2015-136022

(51) Int. Cl.
*G01N 1/38*     (2006.01)
*G01N 35/10*    (2006.01)
(Continued)

(52) U.S. Cl.
CPC .............. *G01N 35/04* (2013.01); *G01N 1/38* (2013.01); *G01N 21/64* (2013.01); *G01N 33/543* (2013.01);
(Continued)

(58) Field of Classification Search
USPC ........................................................ 436/177
See application file for complete search history.

(56) References Cited

U.S. PATENT DOCUMENTS 5,452,619 A * 9/1995 Kawanabe ........... G01N 33/491
                                                73/863
5,555,767 A * 9/1996 Makino .................... G01N 1/38
                                                436/175
(Continued)

FOREIGN PATENT DOCUMENTS

JP     62-184356     8/1987
JP     62-184357     8/1987
(Continued)

OTHER PUBLICATIONS

Reasons for Rejection dated Nov. 26, 2019 issued in Japanese Patent Application No. 2017-527481.
(Continued)

*Primary Examiner* — Matthew D Krcha
*Assistant Examiner* — Brittany I Fisher
(74) *Attorney, Agent, or Firm* — Sughrue Mion, PLLC (57) ABSTRACT

A detection device for detecting a substance to be detected contained in a specimen has a pipette that has a detachable pipette tip and that suctions or discharges a specimen in a container, a pipette-moving unit for moving the pipette, and a control unit for controlling the pipette and pipette-moving unit. The control unit controls the pipette and the pipette-moving unit so that the pipette suctions a portion of specimen in the container with the pipette-moving unit having moved the distal end of the pipette tip to a position (a) in the lower side of the container, and thereafter discharges in the container the specimen suctioned by the pipette to stir the
(Continued)

specimen with the pipette-moving unit having moved the distal end of the pipette tip to a position (b) above the position (a).

16 Claims, 6 Drawing Sheets

(51) Int. Cl.
    *G01N 21/64*     (2006.01)
    *G01N 35/04*     (2006.01)
    *G01N 35/02*     (2006.01)
    *G01N 33/543*     (2006.01)

(52) U.S. Cl.
    CPC ............. *G01N 35/02* (2013.01); *G01N 35/10* (2013.01); *G01N 35/1011* (2013.01); *G01N 2035/0434* (2013.01); *G01N 2035/103* (2013.01)

(56) References Cited

U.S. PATENT DOCUMENTS

| | | | |
|---|---|---|---|
| 6,100,079 A | 8/2000 | Tajima | |
| 6,691,748 B1 | 2/2004 | Tajima | |
| 6,805,840 B1 | 10/2004 | Tajima | |
| 2009/0316519 A1* | 12/2009 | Gorka | ................... B01F 3/0865 366/140 |
| 2014/0118747 A1* | 5/2014 | Aoki | ...................... G01N 21/64 356/445 |
| 2017/0205321 A1* | 7/2017 | Sasaki | ..................... B01F 15/02 |

FOREIGN PATENT DOCUMENTS

| | | |
|---|---|---|
| JP | 10-307141 | 11/1998 |
| JP | 2011-107089 | 6/2011 |
| WO | WO 1997/044671 | 11/1997 |
| WO | WO 2011/074273 | 6/2011 |

OTHER PUBLICATIONS

Preliminary Report on Patentability and Written Opinion dated Jan. 9, 2018 which issued in International Patent Application No. PCT/JP2016/070047.

Search Report dated Jun. 26, 2018 issued in the corresponding European Patent Application No. 16821438.5.

Decision of Refusal dated Mar. 10, 2020 issued in Japanese Patent Application No. 2017-527481.

* cited by examiner

DETECTION DEVICE AND DETECTION METHOD

RELATED APPLICATIONS

This is a U.S. National Phase Application under 35 USC 371 of International Application PCT/JP2016/070047 filed on Jul. 6, 2016.

This application claims the priority of Japanese application no. 2015-136022 filed Jul. 7, 2015, the entire content of which is hereby incorporated by reference.

TECHNICAL FIELD

The present invention relates to a detection apparatus and a detection method.

BACKGROUND ART

In a clinical test or the like, highly sensitive and quantitative detection of a trace amount of analyte, such as a protein or DNA, in blood or other specimens would enable quick understandings of patients' conditions and their subsequent treatment. For this reason, there is a need for a method and an apparatus that can detect a trace amount of analyte in a specimen highly sensitively and quantitatively.

A surface plasmon resonance (hereinafter, abbreviated as "SPR") method and surface plasmon-field enhanced fluorescence spectroscopy (hereinafter, abbreviated as "SPFS") are known as methods that can detect analytes in specimens highly sensitively. These methods exploit the phenomenon of surface plasmon resonance (SPR) occurring upon irradiation of a metal film with light under predetermined conditions (see, Patent Literature (hereinafter, abbreviated as PTL) 1, for example).

In SPFS, for example, a capturing body (primary antibody, for example) that can specifically bind to an analyte is immobilized on a metal film, thereby forming a reaction site for specific capturing of the analyte. When a specimen (blood, for example) containing an analyte is provided to the reaction site, the analyte binds to the reaction site. Subsequently, when a capturing body (secondary antibody, for example) labeled with a fluorophore is provided to the reaction site, the analyte that has bound to the reaction site is labeled with the fluorophore. Under such conditions, when the metal film is irradiated with excitation light, the fluorophore that labels the analyte is excited with SPR-enhanced electric fields, thereby emitting fluorescence. Accordingly, the presence or the amount of the analyte is detected by detecting fluorescence. Since the fluorophore is excited with SPR-enhanced electric fields in SPFS, the analyte can be detected highly sensitively.

When an analyte in a liquid is measured by various detection methods, as well as a SPR method and SPFS, the detection value is typically expressed as the mass of the analyte per unit volume of the liquid or the corresponding signal intensity, for example. When a specimen is blood, the detection value is expressed as the mass of the analyte per unit volume of liquid components in blood (blood plasma or serum) or the corresponding signal intensity, for example. Since proportions of liquid components in blood vary among individuals, detected values of blood cannot be converted uniformly to liquid component-based detection values. Therefore, when a specimen is blood, a detected value of blood is converted to a liquid component (blood plasma or serum)-based detection value using a separately measured hematocrit (volume proportion of blood cells in blood).

Meanwhile, blood cells tend to precipitate after blood is left standing for a certain time. Accordingly, when it takes long to perform detection after a user sets blood in a container, blood cells precipitate and thus a hematocrit tends to fluctuate depending on positions where blood is collected. Consequently, the hematocrit of collected blood deviates from the original value, and thus the amount of an analyte in liquid components cannot be detected accurately in some cases.

In order to suppress precipitation of blood cells, stirring of blood before detection is considered to be effective. As an apparatus equipped with a stirring mechanism, there is known an immunoassay apparatus that stirs a specimen by repeating drawing and discharging of the specimen while a leading end of a pipette tip for transferring reagents is fixed near a bottom surface of a container (see PTL 2, for example).

CITATION LIST

Patent Literature

PTL 1
Japanese Patent Application Laid-Open No. H10-307141
PTL 2
WO 1997/044671

SUMMARY OF INVENTION

Technical Problem

A stirring method, such as the method disclosed in PTL 2, however, cannot obtain satisfactory stirring effects.

Further, when the amount of a specimen that a user sets in a container and the volume of a pipette tip differ largely, the following problems arise. For example, when a pipette tip that can draw 100 μL is used and the amount of a specimen set in a container is 500 μL, drawing and discharging of only 100 μL can hardly stir the specimen. Meanwhile, when a pipette that can draw 500 μL is used and the amount of a specimen set in a container is only 100 μL, air is also readily drawn into. Accordingly, such stirring results in incorporation of a large amount of air bubbles inside the container, and thus quantitative performance during collecting of the specimen cannot be ensured. Moreover, the use of a pipette that can draw 500 μL also involves an issue of growing size of an apparatus. Therefore, it is desired that a specimen inside a container can be stirred satisfactorily even when the amount of a specimen set in the container and the volume of a pipette tip differ largely.

An object of the present invention is to provide a detection apparatus and a detection method that can stir a specimen satisfactorily and detect an analyte contained in the specimen accurately.

Solution to Problem

To achieve at least one of the above-mentioned objects, a detection apparatus according to an embodiment of the present invention for detecting an analyte contained in a specimen, includes: a pipette that allows a pipette tip to be detached therefrom, and that draws or discharges a specimen inside a container; a pipette moving section that moves the pipette; and a control section that controls the pipette and the pipette moving section, in which; the control section controls the pipette and the pipette moving section so as to stir the specimen by causing the pipette to draw at least part of the specimen inside the container in a state after a leading end of the pipette tip is moved to position A on a lower side of the container by the pipette moving section, and then the pipette to discharge the drawn specimen to the inside of the container in a state after the leading end of the pipette tip is moved to position B above position A by the pipette moving section.

To achieve at least one of the above-mentioned objects, a detection method according to the embodiment of the present invention includes: stirring a specimen inside a container by drawing at least part of the specimen inside the container by the pipette in a state after a leading end of a pipette tip fixed to the pipette is moved to position A on a lower side of the container, and then discharging the drawn specimen by the pipette in a state after the leading end of the pipette tip is moved to position B above position A; and detecting an analyte contained in the stirred specimen.

Advantageous Effects of Invention

The present invention can provide a detection apparatus and a detection method that can stir a specimen satisfactorily and detect an analyte contained in the specimen accurately.

BRIEF DESCRIPTION OF DRAWINGS

FIG. 4A is a graph indicating an example relationship between time for allowing blood to stand inside a container and hematocrit of blood collected on a lower side of the container after the standing, whereas

DESCRIPTION OF EMBODIMENTS

Embodiments of the present invention will be described in detail hereinafter with reference to the accompanying drawings. As a representative example of a detection apparatus according to the present invention, a detection apparatus (SPFS apparatus) utilizing surface plasmon-field enhanced fluorescence spectroscopy (hereinafter, abbreviated as "SPFS") will be described.

[Configurations of SPFS Apparatus and Detection Chip]

Figure 1:
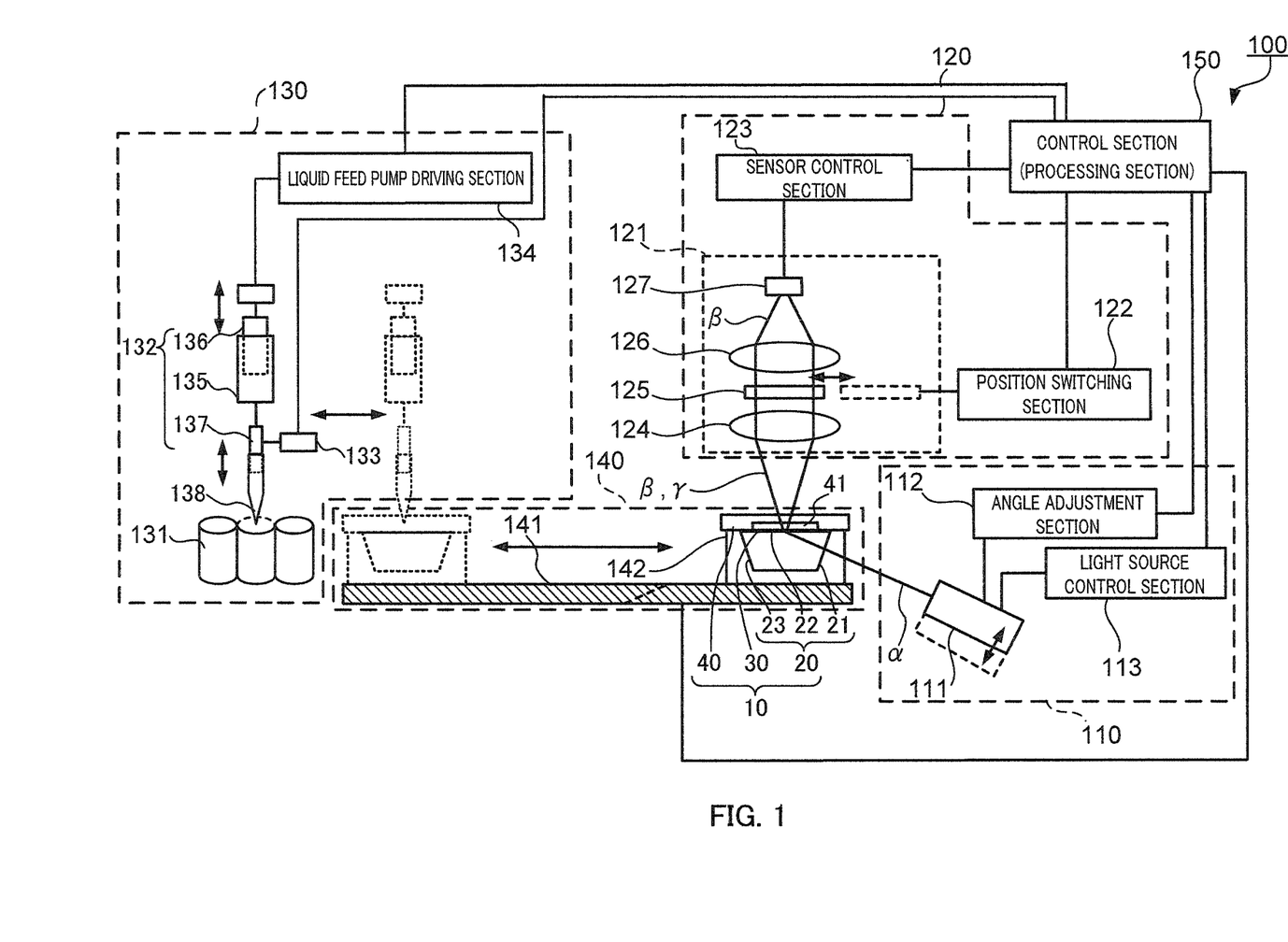
FIG. 1 is a schematic view illustrating a configuration of a SPFS apparatus according to an embodiment.

FIG. 1 is schematic view illustrating a configuration of SPFS apparatus 100 according to the embodiment. As illustrated in FIG. 1, SPFS apparatus 100 includes light irradiation section 110, light detection section 120, liquid feed section 130, conveyance section 140, and control section 150. SPFS apparatus 100 is used while detection chip 10 is mounted on chip holder (holder) 142 in conveyance section 140. First, detection chip 10 will be described, followed by the description of SPFS apparatus 100.

(Detection Chip)

Detection chip 10 includes: prism 20 having incident surface 21, film forming surface 22, and emission surface 23; metal film 30 on which a capturing body for capturing an analyte is immobilized, disposed on film forming surface 22; and channel lid 40 disposed on metal film 30. Detection chip 10 is preferably a structure with a length of several millimeters to several centimeters, but may be a smaller structure or a larger structure, which is excluded from the category of "chip."

Prism 20 is made from a dielectric transparent to excitation light α. Prism 20 has incident surface 21, film forming surface 22, and emission surface 23. Excitation light α from light irradiation section 110 enters inside prism 20 from incident surface 21. Metal film 30 is disposed on film forming surface 22. Excitation light α that enters inside prism 20 is reflected on a rear surface of metal film 30 as reflected light (not shown). More specifically, excitation light α is reflected, as reflected light, at the interface (film forming surface 22) between prism 20 and metal film 30. The reflected light is emitted outside prism 20 from emission surface 23.

The shape of prism 20 is not limited. In the embodiment, the shape of prism 20 is a trapezoidal prism. The surface corresponding to either the bases of the trapezoid is film forming surface 22, the surface corresponding to either the legs is incident surface 21, and the surface corresponding to the other leg is emission surface 23. The trapezoid as a base is preferably an isosceles trapezoid. This makes incident surface 21 and emission surface 23 symmetrical, thereby suppressing confinement of s-wave component of excitation light α inside prism 20.

Incident surface 21 is formed so that excitation light α does not return to light irradiation section 110. When a light source for excitation light α is a laser diode (hereinafter, also referred to as "LD"), returned excitation light α to LD would disturb the excitation state of the LD and alter a wavelength and/or an output of excitation light α. Accordingly, the angle of incident surface 21 is set within an ideal scanning range centered on a resonance angle or an enhanced angle such that excitation light α does not enter incident surface 21 perpendicularly.

The term "resonance angle" herein indicates an incident angle at which quantity of reflected light from emission surface 23 becomes minimum during scanning of incident angles of excitation light α on metal film 30. Meanwhile, the term "enhanced angle" herein indicates an incident angle at which quantity of scattered light γ with the same wavelength as excitation light α emitted above detection chip 10 (hereinafter, referred to as "plasmon scattered light") becomes maximum during scanning of incident angles of excitation light α on metal film 30. In the embodiment, both the angle between incident surface 21 and film forming surface 22, and the angle between film forming surface 22 and emission surface 23 are about 80°.

A resonance angle (and an enhanced angle in the immediate vicinity thereof) is basically determined by the design of detection chip 10. Design factors include a refractive index of prism 20, a refractive index of metal film 30, a thickness of metal film 30, an extinction coefficient of metal film 30, and a wavelength of excitation light α, for example. Although a resonance angle and an enhanced angle are shifted by an analyte captured on metal film 30, the shift is less than several degrees.

Prism 20 exhibits not a little birefringence characteristics. Examples of materials for prism 20 include a resin and glass.

The material for prism 20 is preferably a resin having a refractive index of 1.4 to 1.6 and small birefringence.

Metal film 30 is disposed on film forming surface 22 of prism 20. Due to this, surface plasmon resonance (hereinafter, abbreviated as "SPR") can be generated between photons of excitation light α incident on film forming surface 22 under total reflection conditions and free electrons in metal film 30, thereby generating localized-field light (generally called "evanescent light" or "near-field light") above the surface of metal film 30. In the embodiment, metal film 30 is formed on the entire film forming surface 22.

Materials for metal film 30 are not limited as long as they are metals that can generate surface plasmon resonance. Examples of the materials for metal film 30 include gold, silver, copper, aluminum, and an alloy thereof. In the embodiment, metal film 30 is a gold thin film. The method of forming metal film 30 is not limited. Examples of the methods of forming metal film 30 include sputtering, vapor deposition, and plating. The thickness of metal film 30 is not limited, but is preferably within the range of 30 to 70 nm.

A capturing body for capturing an analyte is immobilized on the surface of metal film 30 facing away from prism 20. The type of capturing body is not limited as long as an analyte can be captured. The capturing body is, for example, an antibody that binds to the analyte specifically or a fragment thereof. From a viewpoint of preventing denaturation due to drying, the capturing body is typically stored using a protective layer before use of detection chip 10.

Channel lid 40 is disposed on metal film 30. When metal film 30 is only partially formed on film forming surface 22 of prism 20, channel lid 40 may be disposed on film forming surface 22. In the embodiment, channel lid 40 is disposed on metal film 30. By disposing channel lid 40 on metal film 30, a reservoir portion (micro-space) for holding a liquid is formed. The shape and the size of the reservoir portion are not limited as long as a liquid can be held. The reservoir portion may be, for example, a well for holding a liquid or a channel to which a liquid is continuously supplied. In the embodiment, the reservoir portion is channel 41, in which a liquid flows. Channel 41 is formed by disposing, on metal film 30 (and prism 20), channel lid 40 on whose rear surface channel grooves are formed. Metal film 30, on which a capturing body for capturing an analyte is immobilized, is exposed on the bottom surface of channel 41. Both ends of channel 41 are each connected with an inlet port and an outlet port (neither shown) formed on the top surface of channel lid 40.

Channel lid 40 is preferably made from a material transparent to fluorescence β and plasmon scattered light γ emitted from metal film 30. Examples of the materials for channel lid 40 include glass and a resin. As long as a portion, through which fluorescence β and plasmon scattered light γ are extracted outside, is transparent to fluorescence β and plasmon scattered light γ, other portions of channel lid 40 may be made from an opaque material. Channel lid 40 is joined to metal film 30 or prism 20, for example, through bonding using a double-stick tape, an adhesive, or the like, laser welding, ultrasonic welding, or pressure bonding using a clamping member.

By irradiating metal film 30 of detection chip 10 with excitation light α at an angle for generating SPR, localized-field light can be generated above metal film 30. A fluorophore that labels an analyte present above metal film 30 is excited by localized-field light, thereby emitting fluorescence β near the surface of metal film 30 on the side of channel 41. SPFS apparatus 100 can measure an analyte by measuring quantity of fluorescence β emitted from the fluorophore.

(SPFS Apparatus)

In the following, each component of SPFS apparatus 100 will be described. As already mentioned, SPFS apparatus 100 includes light irradiation section 110, light detection section 120, liquid feed section 130, conveyance section 140, and control section 150.

Light irradiation section 110 irradiates detection chip 10 held in chip holder 142 with excitation light α. During detection of fluorescence β or plasmon scattered light γ, light irradiation section 110 emits only p-wave (relative to metal film 30) to incident surface 21 so as to generate SPR in metal film 30. As used herein, the term "excitation light" is light for generating plasmon scattered light γ above metal film 30, and is also light for exciting a fluorophore directly or indirectly. Light irradiation section 110 includes light source unit 111, angle adjustment section 112, and light source control section 113.

Light source unit 111 emits collimated light having a constant wavelength and light quantity such that the shape of an irradiation spot on the rear surface of metal film 30 becomes nearly circular. Light source unit 111 includes, for example, a light source, a beam shaping optical system, an APC mechanism, and a temperature adjustment section (neither shown).

The type of light source is not limited, and is a laser diode (LD), for example. Other examples of the light sources include a light-emitting diode, a mercury lamp, and other laser light sources. When excitation light α emitted from the light source is not a beam, excitation light α is converted to a beam by a lens, a mirror, and/or a slit, for example. Moreover, when excitation light α emitted from the light source is not monochromatic light, excitation light α is converted to monochromatic light by a diffraction grating, for example. Further, when excitation light α emitted from the light source is not linearly polarized light, excitation light α is converted to linearly polarized light by a polarizer, for example.

The beam shaping optical systems include a collimator, a bandpass filter, a linear polarizing filter, a half-wave plate, a slit, and a zoom unit, for example. The beam shaping optical system may include all of them or some of them. A collimator collimates excitation light α emitted from the light source. A bandpass filter converts excitation light α emitted from the light source to narrow-band light solely consisting of the central wavelength since excitation light α emitted from the light source has some wavelength distribution widths. A linear polarizing filter converts excitation light α emitted from the light source to completely linearly polarized light. A half-wave plate adjusts the polarization direction of light such that the p-wave component is incident on metal film 30. A slit and a zoom unit adjust the beam diameter or the contour shape of excitation light α emitted from the light source such that the shape of an irradiation spot on the rear surface of metal film 30 becomes circular of a predetermined size.

The APC mechanism controls the light source such that an output of the light source becomes constant. More specifically, the APC mechanism detects quantity of light split from excitation light α using a photodiode (not shown), for example. The APC mechanism thus controls an output of the light source at a constant value by controlling input energy with a feedback circuit.

A temperature adjustment section is a heater or a Peltier device, for example. The wavelength and the energy of excitation light α emitted from the light source fluctuate depending on the temperature in some cases. Accordingly, the wavelength and the energy of excitation light α emitted from the light source are controlled at constant values by maintaining a constant temperature of the light source by the temperature adjustment section.

Angle adjustment section 112 adjusts an incident angle of excitation light α emitted from the light source on metal film 30 (interface (film forming surface 22) between prism 20 and metal film 30). Angle adjustment section 112 relatively rotates the optical axis of excitation light α emitted from the light source and chip holder 142 so as to irradiate a predetermined position of metal film 30 with light at a predetermined incident angle through prism 20.

Angle adjustment section 112, for example, turns light source unit 111 around an axis orthogonal to the optical axis of excitation light α emitted from the light source (an axis perpendicular to the plane of FIG. 1). During this operation, the position of the rotational axis is set so that the position of an irradiation spot on metal film 30 changes little even during scanning of incident angles. In particular, displacement of the irradiation position can be minimized by setting the position of the rotation center in the vicinity of an intersection of optical axes of excitation light α emitted from the light source at both the edges of the scanning range of incident angles (between the irradiation position on film forming surface 22 and incident surface 21).

As mentioned above, an angle at which quantity of plasmon scattered light γ becomes maximum is an enhanced angle, among incident angles of excitation light α emitted from the light source on metal film 30. By setting the incident angle of excitation light α emitted from the light source to an enhanced angle or an angle in the vicinity thereof, detection of high-intensity fluorescence β and plasmon scattered light γ becomes possible. Basic incidence conditions of excitation light α emitted from the light source are determined by the material and shape of prism 20, a thickness of metal film 30, and a refractive index of the liquid inside channel 41, for example. Optimal incidence conditions, however, slightly vary depending on the type and the amount of capturing body inside channel 41, as well as an error in the shape of prism 20, for example. Accordingly, the optimal enhanced angle is preferably obtained for every detection.

Light source control section 113 controls emission of excitation light α from light source unit 111 by controlling various types of equipment included in light source unit 111. Light source control section 113 is formed from, for example, a commonly known computer or a microcomputer including an arithmetic device, a control device, a storage device, an input device, and an output device.

Light detection section 120 detects light emitted from detection chip 10 upon irradiation of metal film 30 with light by light irradiation section 110. Light detection section 120 detects plasmon scattered light γ that passes through channel 41 as well as fluorescence β emitted from a fluorophore in a reaction site upon irradiation of metal film 30 of detection chip 10 with excitation light α by light irradiation section 110. Light detection section 120 includes light-receiving optical system unit 121, position switching section 122, and sensor control section 123.

Light-receiving optical system unit 121 is disposed in the normal direction to metal film 30 of detection chip 10. Light-receiving optical system unit 121 includes first lens 124, optical filter 125, second lens 126, and light-receiving sensor 127.

First lens 124 is a condensing lens, for example, and focuses light emitted from above metal film 30. Second lens 126 is an imaging lens, for example, and forms an image of light focused by first lens 124 on a light-receiving surface of light-receiving sensor 127. The optical paths between the lenses are nearly parallel. Optical filter 125 is disposed between the lenses.

Optical filter 125 guides a fluorescence component alone to light-receiving sensor 127 while removing an excitation light component (plasmon scattered light γ) so as to detect fluorescence β at a high S/N ratio. Examples of optical filter 125 include an excitation light-reflective filter, a short wavelength-blocking filter, and a bandpass filter. Optical filter 125 is, for example, a filter containing a multilayer film that reflects a predetermined light component (light with a predetermined wavelength component) or a color glass filter that absorbs a predetermined light component.

Light-receiving sensor 127 detects fluorescence β and plasmon scattered light γ. Light-receiving sensor 127 has high sensitivity so that faint fluorescence β from a trace amount of analyte can be detected. Light-receiving sensor 127 is a photomultiplier tube (PMT) or an avalanche photodiode (APD), for example Position switching section 122 switches positions of optical filter 125 from on to off and vice versa the optical path of light-receiving optical system unit 121. Specifically, when light-receiving sensor 127 detects fluorescence β, optical filter 125 is disposed on the optical path of light-receiving optical system unit 121, whereas when light-receiving sensor 127 detects plasmon scattered light γ, optical filter 125 is disposed off the optical path of light-receiving optical system unit 121.

Sensor control section 123 controls, for example, detection of output values in light-receiving sensor 127, sensitivity management in light-receiving sensor 127 using detected output values, and change of sensitivity in light-receiving sensor 127 for obtaining suitable output values. Sensor control section 123 is formed from, for example, a commonly known computer or a microcomputer including an arithmetic device, a control device, a storage device, an input device, and an output device.

Liquid feed section 130 supplies various liquids, such as a specimen, a labeling solution, and a rinse solution, inside channel 41 of detection chip 10 held in chip holder 142. When a specimen tends to exhibit a concentration distribution after standing for a certain time, liquid feed section 130 preferably further stirs the specimen inside container 131. Liquid feed section 130 includes pipette 132 that draws or discharges a liquid inside container 131, pipette moving section 133 that moves pipette 132, and liquid feed pump driving section 134.

Containers 131 are containers for holding various liquids. In general, as containers 131, a plurality of containers are disposed corresponding to the types of liquids, or an integrated chip of a plurality of containers is disposed.

Examples of the liquids held in containers 131 include a specimen containing an analyte (blood, diluted blood, serum, blood plasma, urine, nostril mucus, saliva, or semen, for example), a labeling solution containing a capturing body labeled with a fluorophore, and a rinse solution (buffer solution), and a modeling solution for calibration of apparatuses (mixture of a plurality of buffer solutions with different specific gravities). Examples of liquids for diluting blood include a phosphate-buffered saline (PBS), Tris [tris(hydroxymethyl)aminomethane] (TBS: Tris-buffered saline), and HEPES [2-[4-(2-hydroxyethyl)-1-piperazinyl]

ethanesulfonic acid]. Such liquids further containing Tween 20 surfactant are used in some cases.

Pipette 132 includes syringe 135, plunger 136 that can reciprocate inside syringe 135, and pipette nozzle 137 connected with syringe 135. A liquid is quantitatively drawn and discharged by the reciprocating motion of plunger 136. Pipette tip 138 is fixed to pipette nozzle 137.

Pipette moving section 133 freely moves pipette 132 or pipette nozzle 137 in the axial direction of pipette 132 (vertical direction, for example) as well as the direction crossing the axial direction (horizontal direction, for example). Pipette moving section 133 is formed from a robot arm, a two-axis stage, or vertically movable turntable, for example.

Liquid feed pump driving section 134 causes plunger 136 to reciprocate, and thus causes pipette 132 to draw or discharge a liquid. Liquid feed pump driving section 134 includes a stepping motor, for example. A driving apparatus including a stepping motor can regulate a liquid feed volume or a liquid feed rate by pipette 132, and thus is preferred from a viewpoint of regulating a residual liquid volume in detection chip 10.

Liquid feed section 130 supplies a liquid drawn from container 131 to channel 41 of detection chip 10. After the liquid is supplied to channel 41 of detection chip 10, the liquid is caused to reciprocate inside channel 41 by moving plunger 136, and thus the liquid inside channel 41 can be stirred. This can achieve a uniform concentration distribution of a liquid inside channel 41 and/or promote reactions inside channel 41 (primary reaction and secondary reaction, for example). From a viewpoint of performing such operations, detection chip 10 and pipette 132 are preferably configured to protect an inlet of detection chip 10 with a multilayer film, and to seal the inlet when pipette tip 138 penetrates the multilayer film.

A liquid inside channel 41 is drawn again by pipette 132 and discharged into container 131 or the like. By repeating these operations, reactions by various liquids, washing, and the like can be performed, thereby disposing, for example, an analyte labeled with a fluorophore inside channel 41.

When the specimen tends to generate a concentration distribution after standing for a certain time, liquid feed section 130 preferably further stirs a specimen inside container 131.

A specimen that tends to generate a concentration distribution after standing for a certain time may be a specimen containing a plurality of substances (solid/liquid, liquid/liquid) with different specific gravities. Examples of such specimens include blood, diluted blood, blood plasma, and a modeling solution for calibrating apparatuses (a mixture of a plurality of buffer solutions).

Specifically, control section 150 controls pipette 132 and pipette moving section 133 so as to stir the specimen by causing pipette 132 to draw at least part of a specimen inside container 131 in a state after the leading end of pipette tip 138 is moved to position A on a lower side of container 131 by pipette moving section 133, and then the pipette to discharge the drawn specimen to the inside of container 131 in a state after the leading end of pipette tip 138 is moved to position B above position A (see FIGS. 3A to 3D described hereinafter). The specimen inside container 131 can be stirred satisfactorily by repeating these operations once or more. Consequently, a uniform concentration distribution of a liquid supplied to channel 41 of detection chip 10 can be achieved.

When a specimen inside container 131 is stirred, control section 150 may switch as needed, in accordance with the type or the amount of the specimen, the number of times pipette 132 repeats drawing and discharging of the specimen, and/or positions of the leading end of pipette tip 138 when the specimen is drawn or discharged.

Conveyance section 140 conveys detection chip 10 to a loading position, a detection position, or a liquid feed position, and fixes the chip. The term "loading position" herein indicates a position for loading detection chip 10 on SPFS apparatus 100. The term "detection position" herein indicates a position at which the light detection section 120 detects fluorescence β or plasmon scattered light γ generated upon irradiation of detection chip 10 with light by light irradiation section 110. Further, the term "liquid feed position" herein indicates a position at which liquid feed section 130 supplies a liquid inside channel 41 of detection chip 10, or removes a liquid inside channel 41 of detection chip 10.

Conveyance section 140 includes conveyance stage 141 and chip holder 142. Chip holder 142 is fixed to conveyance stage 141 and holds detection chip 10 detachably. The shape of chip holder 142 is a shape in which detection chip 10 can be held without obstructing optical paths of excitation light α, reflected light, fluorescence β, and plasmon scattered light γ. Chip holder 142 has, for example, an aperture for passing through excitation light α, reflected light, fluorescence β, and plasmon scattered light γ. Conveyance stage 141 moves chip holder 142 in one and the opposite directions. The shape of conveyance stage 141 is also a shape in which optical paths of excitation light α, reflected light, fluorescence β, and plasmon scattered light γ are not obstructed. Conveyance stage 141 is driven by a stepping motor, for example.

Control section 150 controls angle adjustment section 112, light source control section 113, position switching section 122, sensor control section 123, pipette moving section 133, liquid feed pump driving section 134, and conveyance stage 141. Control section 150 also functions as a processing section that processes detected results in light detection section 120 (light-receiving sensor 127). Control section 150 is formed from, for example, a commonly known computer or microcomputer that includes an arithmetic apparatus, a control apparatus, a storage apparatus, an input apparatus, and an output apparatus.

[Detection Operations of SPFS Apparatus]

Figure 2:
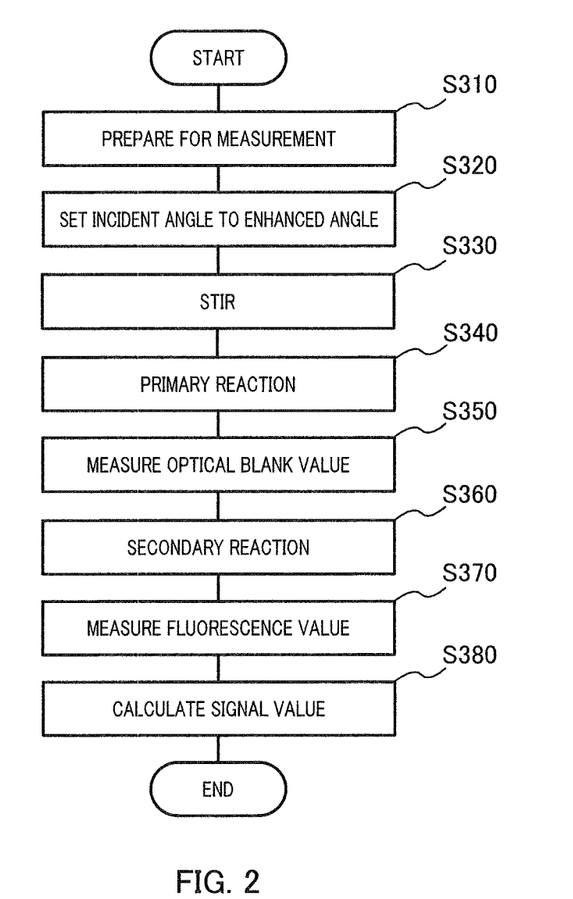
FIG. 2 is a flow chart showing an example operation procedure of the SPFS apparatus according to the embodiment.

In the following, the detection operations of SPFS apparatus 100 according to the embodiment (a detection method according to the embodiment of the present invention) will be described. FIG. 2 is a flow chart showing an example operation procedure of SPFS apparatus 100. The embodiment will be described as an example in which a specimen contains a plurality of substances with different specific gravities.

First, the detection is prepared (step S310). Specifically, detection chip 10 is loaded on chip holder 142 disposed at a loading position of SPFS apparatus 100. Container 131 holding a specimen is also set in SPFS apparatus 100. The amount of the specimen held in container 131 is larger than the dead volume of container 131 and smaller than the maximum volume of container 131. The dead volume herein indicates residual amount inside container 131 that cannot be drawn by pipette 132.

Subsequently, an incident angle of excitation light α emitted from a light source on metal film 30 (film forming surface 22) is set to an enhanced angle (step S320). Specifically, control section 150 controls conveyance stage 141 to cause detection chip 10 to move from the loading position to the detection position. Control section 150 then controls light source control section 113 and angle adjustment section 112 to scan incident angles of excitation light α on metal film 30 (film forming surface 22) while irradiating a predetermined position of metal film 30 (film forming surface 22) with excitation light α from light source unit 111. In this step, control section 150 controls position switching section 122 to cause optical filter 125 and light-receiving optical system unit 121 to move off the optical path. At the same time, control section 150 controls sensor control section 123 to cause light receiving sensor 127 to detect plasmon scattered light γ. Control section 150 obtains data including a relationship between incident angle of excitation light a and intensity of plasmon scattered light γ. Control section 150 then analyzes the data and determines the incident angle (enhanced angle) with the maximum intensity of plasmon scattered light γ. Finally, control section 150 controls angle adjustment section 112 to set an incident angle of excitation light α on metal film 30 (film forming surface 22) to the enhanced angle. The detected values of plasmon scattered light γ during the measurement of the enhanced angle may be recorded in control section 150 as blank values.

The enhanced angle is dependent on the material or the shape of prism 20, the thickness of metal film 30, and the refractive index of a liquid inside channel 41, for example. The enhanced angle, however, slightly changes due to various factors, such as the type and the amount of a liquid inside channel 41 and dimensional errors in prism 20. Accordingly, the enhanced angle is preferably determined for every measurement. The enhanced angle is determined in the order of about 0.1°.

Figure 3A:
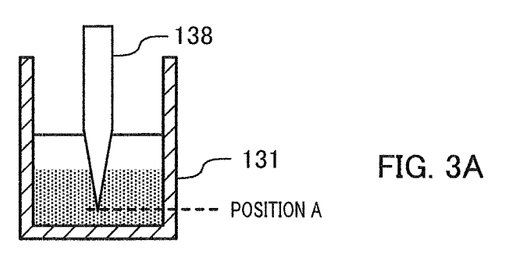
FIGS. 3A to 3D is a schematic view illustrating an example stirring process according to the embodiment.
Figure 3B:
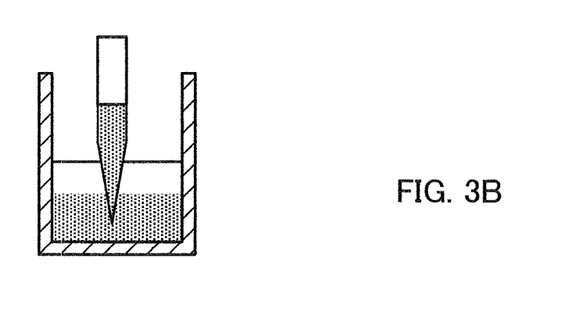

Subsequently, the specimen inside container 131 is stirred (stirring; step S330). FIGS. 3A to 3C are schematic views illustrating an example stirring process according to the embodiment. As illustrated in FIG. 3A, control section 150 controls pipette moving section 133 to cause the leading end of pipette tip 138 to move to position A on a lower side of container 131 (see FIG. 3A). Control section 150 then controls liquid feed pump driving section 134 to cause pipette 132 to draw at least part of the specimen inside container 131 while the leading end of pipette tip 138 is fixed at position A (see FIG. 3B).

"Position A" is a position of the leading end of pipette tip 138 when pipette 132 draws at least part of a specimen inside container 131. Specifically, position A indicates a position in a region where a substance with a relatively high specific gravity is concentrated when a specimen containing a plurality of substances with different specific gravities is left standing inside container 131 for a certain time. When a specimen is blood, the region where a substance with a relatively high specific gravity is concentrated indicates a region where blood cells are precipitated.

Figure 3C:
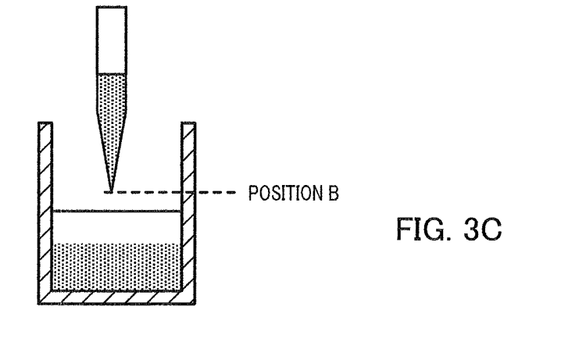

Control section 150 then controls pipette moving section 133 to cause the leading end of pipette tip 138 to move to position B above position A (see FIG. 3C). Control section 150 controls liquid feed pump driving section 134 to cause pipette 132 to discharge the drawn specimen to the inside of container 131 while the leading end of pipette tip 138 is fixed at position B (see FIG. 3D).

Figure 3D:
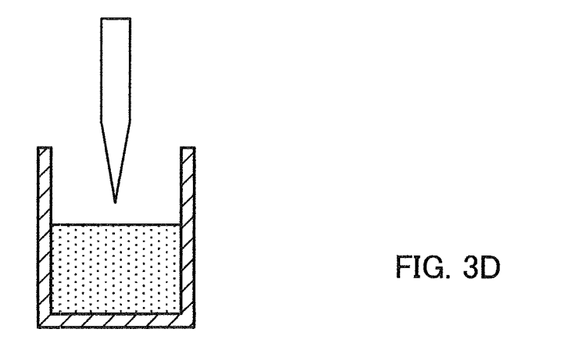

"Position B" is a position of the leading end of pipette tip 138 when the pipette 132 discharges the drawn specimen to the inside of container 131. Specifically, position B indicates a position above a region where a substance with a relatively high specific gravity is concentrated inside container 131 after a specimen containing a plurality of substances with different specific gravities is left standing inside container 131 for a certain time. Position B is preferably above the liquid surface of a specimen inside container 131, and is preferably more than 0 mm and 15 mm or less apart from the liquid surface of the specimen. When position B is 15 mm or less above the liquid surface of the specimen inside container 131, scattering of the specimen in the vicinity of container 131, and resulting soiling of the apparatus can be suppressed. Since pipette 132 discharges the drawn specimen to the inside of container 131 from above the liquid surface of the specimen inside container 131, high stirring effects can be obtained due to collisions at gas-liquid interfaces.

Position A and position B vary depending on the type or the amount of the specimen, the shape of container 131, or the like. For example, position A may be set to ⅓ or less the height of container 131 from the bottom surface of container 131; and position B may be set to more than ⅓ the height of container 131 from the bottom surface of container 131.

Pipette moving section 133 preferably moves pipette 132 in the vertical direction. When pipette 132 discharges the drawn specimen, the leading end of pipette tip 138 is preferably positioned so that the specimen is discharged to a central portion of the liquid surface of the specimen inside container 131. The central portion of the liquid surface of the specimen inside container 131 indicates a region within radius r from the center of the liquid surface as the center of a circle. Radius r can be ½ and preferably ⅓ the shortest distance between the center of the liquid surface and the inner wall surface of container 131.

The amount of the specimen drawn or discharged by pipette 132 is 20% by volume or more, and preferably 50% by volume or more of the specimen held in container 131. By setting the amount of a specimen drawn or discharged to a certain amount or more, high stirring effects can be readily obtained since a proportion of the specimen flowing inside container 131 increases.

A discharge rate when the pipette 132 discharges the drawn specimen is preferably 1,000 to 15,000 µL/min By setting the discharge rate to a certain rate or higher, high stirring effects can be readily obtained since a flow rate of the specimen flowing inside container 131 increases.

By repeating the operations in FIGS. 3A to 3D once or more, preferably a plurality of times, the specimen inside container 131 can be stirred satisfactorily.

Subsequently, an analyte in the specimen and a capturing body on metal film 30 are reacted (primary reaction; step S340). Specifically, control section 150 controls conveyance stage 141 to cause detection chip 10 to move from the detection position to the liquid feed position. Control section 150 then controls the liquid feed pump driving section 134 to supply the specimen inside container 131 to the inside of channel 41. If an analyte is present in the specimen, at least part of the analyte is captured by the capturing body on metal film 30 through this operation. After that, the inside of channel 41 is washed with a buffer solution or the like to remove uncaptured substances by the capturing body.

Metal film 30 (film forming surface 22) is then irradiated with excitation light α through prism 20, and the quantity of light with the same wavelength as fluorescence β (optical blank value) is measured (step S350). The "optical blank value" herein indicates the quantity of background light measured together with fluorescence β during the measurement of fluorescence values (step S370). Specifically, control section 150 controls conveyance stage 141 to cause detection chip 10 to move from the liquid feed position to the detection position. Control section 150 controls position switching section 122 to cause optical filter 125 to move on the optical path of light-receiving optical system unit 121. Control section 150 then controls light source control section 113 to cause light source unit 111 to emit excitation light α toward metal film 30 (film forming surface 22). Simultaneously, control section 150 controls sensor control section 123 to cause light-receiving sensor 127 to detect the quantity of light with the same wavelength as fluorescence β. Through this operation, light-receiving sensor 127 can measure the quantity of light αs noise (optical blank value) accurately. The measured value is transmitted to control section 150 and recorded as an optical blank value.

Subsequently, the analyte captured by the capturing body on metal film 30 is labelled with a fluorophore (secondary reaction; step S360). Specifically, control section 150 controls conveyance stage 141 to cause detection chip 10 to move from the detection position to the liquid feed position. Control section 150 then controls the liquid feed pump driving section 134 to supply a fluorescence labeling solution inside container 131 into the inside of channel 41. Through this operation, the analyte can be labeled with the fluorophore. The fluorescence labeling solution is a buffer solution containing an antibody labeled with a fluorophore (secondary antibody), for example. After that, the inside of channel 41 is washed with a buffer solution or the like to remove free fluorophore, for example.

Subsequently, metal film 30 (film forming surface 22) is irradiated with excitation light α through prism 20 while the analyte labeled with the fluorophore is present on the bottom surface of channel 41 (metal film 30) directly or indirectly, and a fluorescence value from the fluorophore that labels the analyte in the reaction site is measured (step S370). Specifically, control section 150 controls conveyance stage 141 to cause detection chip 10 to move from the liquid feed position to the detection position. Control section 150 then controls light source control section 113 to cause light source unit 111 to emit excitation light α toward metal film 30 (film forming surface 22). Simultaneously, control section 150 controls sensor control section 123 to cause light-receiving sensor 127 to detect the quantity of light with the same wavelength as fluorescence β. Through this operation, light-receiving sensor 127 can measure the quantity of fluorescence accurately. The measured value is transmitted to control section 150 and recorded as a fluorescence value.

Finally, a signal value that represents the presence or the amount of the analyte is calculated (step S380). The fluorescence value mainly includes a fluorescence component originated from the fluorophore that labels the analyte (signal value) and an optical blank value. Accordingly, control section 150 can calculate a signal value correlated with the amount of the analyte by subtracting the optical blank value obtained in step S350 from the fluorescence value obtained in step S370. The signal value is converted to the amount or the concentration of the analyte using a calibration curve prepared in advance.

(Advantages)

As described above, in the detection method and SPFS apparatus 100 of the embodiment, a specimen is stirred satisfactorily inside container 131, and then supplied to inside channel 41 of detection chip 10 in an amount required for the primary reaction. Therefore, the amount of an analyte contained in the specimen can be detected accurately since the concentration distribution of the specimen supplied to inside channel 41 of detection chip 10 does not differ largely from the original concentration distribution of the specimen.

Figure 4A:
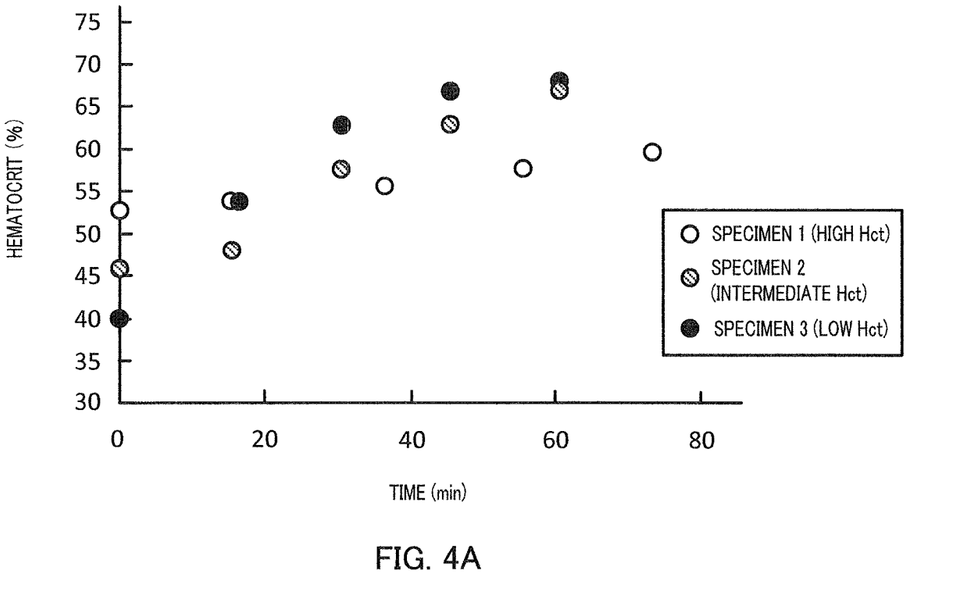
Figure 4B:
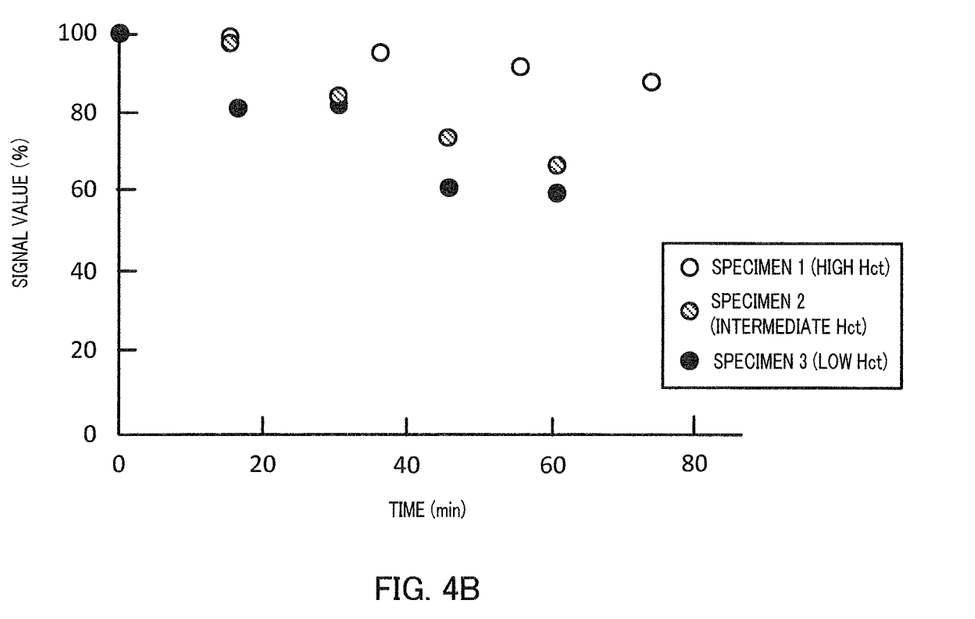
FIG. 4B is a graph indicating an example relationship between time for allowing blood to stand inside a container and signal value of blood collected on a lower side of the container after the standing.

The advantages achieved by the embodiment will be described specifically with an example of blood as a specimen. First, a case without performing a stirring step of a specimen inside container 131 (step S330, for example) will be described. FIG. 4A is a graph indicating an example relationship between time for allowing blood to stand inside container 131 and hematocrit of blood collected on a lower side of container 131 after the standing. FIG. 4B is a graph indicating an example relationship between time for allowing blood to stand inside container 131 and signal value of blood collected on a lower side of the container after the standing. The signal value (%) of FIG. 4B represents a relative value by setting a signal value when the standing time of blood is 0 minute (a signal value in a state without precipitation of blood cells) to 100%. It is shown that the hematocrit of collected blood increases (see FIG. 4A) and the signal value lowers (see FIG. 4B) as the standing time of blood becomes longer. The increase in the hematocrit is presumably because spontaneous precipitation of blood cells progresses over time. The lowering in the signal value is presumably because a proportion of liquid components containing the analyte decreases as the hematocrit of collected blood increases. This trend is shown to be noticeable in specimens with a low hematocrit.

Figure 5:
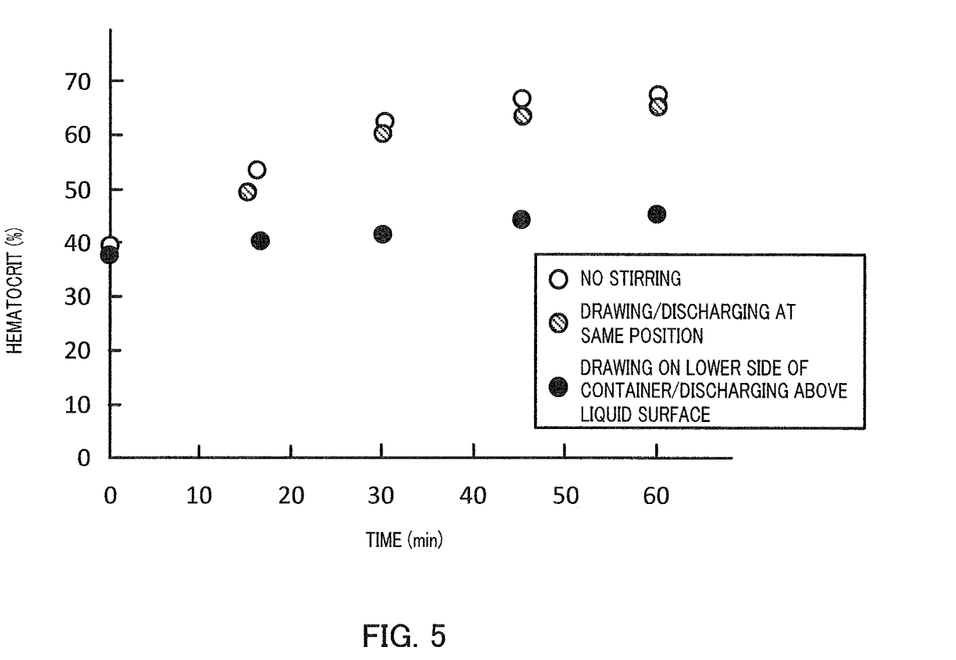
FIG. 5 is a graph indicating an example relationship between time for allowing blood to stand inside a container and hematocrit of blood collected on a lower side of the container.

Next, a case of performing a stirring step of a specimen inside container 131 (step S330, for example) will be described. FIG. 5 is a graph indicating example relationships between time for allowing blood to stand inside container 131 and hematocrit of blood collected on a lower side of container 131. As shown in FIG. 5, it is shown that the hematocrit of collected blood increases when the standing time of blood becomes long in a case without performing stirring or a case of performing drawing and discharging of blood while the leading end of a pipette tip is fixed on a lower side of the container. In contrast, it is shown that the hematocrit of collected blood is nearly constant even if the standing time of blood becomes long in a case of performing stirring of the specimen inside container 131 (step S330). These results reveal that an amount of the analyte in blood can be detected accurately since a proportion of liquid components in blood supplied to detection chip 10 does not differ largely from the original proportion of liquid components.

In particular, in the stirring step of the specimen inside container 131 (step S330), high stirring effects are readily obtained due to collisions at gas-liquid interfaces by discharging drawn specimen while the leading end of pipette tip 138 is disposed above the liquid surface of the specimen inside container 131. Meanwhile, when the volume of pipette tip 138 is larger than the amount of the specimen inside container 131, air tends to be also drawn inside pipette tip 138. By discharging drawn specimen while the leading end of pipette tip 138 is disposed at a position above the liquid surface of the specimen inside container 131, incorporation of air bubbles into the specimen inside container 131 can be suppressed. Accordingly, even when the amount of the specimen inside container 131 and the volume of pipette tip 138 differ largely, satisfactory stirring is possible without incorporating air bubbles into the specimen inside container 131. A case in which the amount of specimen inside container 131 and the volume of pipette tip 138 differ largely herein indicates a case in which a ratio of the pipette tip volume to the amount of specimen inside container 131, or a ratio of the amount of specimen inside container 131 to the volume of pipette tip is a range of 2/1 to 5/1.

In the above embodiment, the detection apparatus and the detection method in which container 131 and detection chip 10 are separate components are described. The detection apparatus and the detection method of the present invention are not limited to such a mode, and an integrated chip of container 131 and detection chip 10 may be employed.

In the above embodiment, the detection apparatus and the detection method in which pipette moving section 133 moves pipette 132 relative to conveyance stage 141. The detection apparatus and the detection method of the present invention are not limited to such a mode, and conveyance stage 141 may be moved relative to pipette 132. For example, in step S330, the specimen inside container 131 may be stirred by moving conveyance stage 141 in the vertical direction while pipette 132 is fixed.

Figure 6:
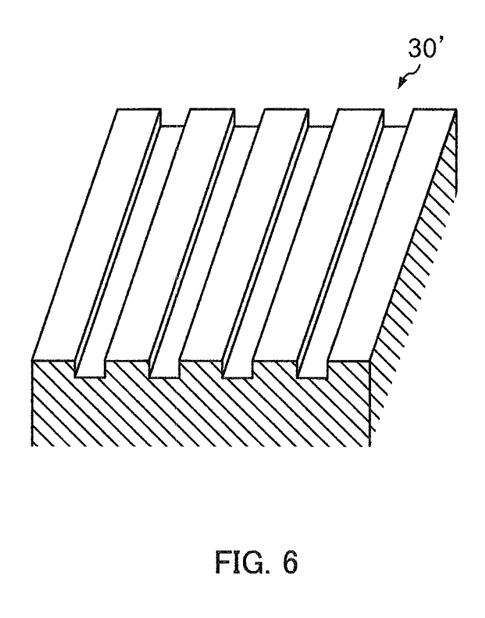
FIG. 6 is a perspective view of a metal film including a diffraction grating.

In the above embodiment, the detection apparatus and the detection method utilizing prism-coupled (PC)-SPFS, in which photons and surface plasmon are coupled using prism 20 on which metal film 30 is formed, are described. The detection apparatus and the detection method of the present invention, however, are not limited to such a mode. FIG. 6 is a perspective view of metal film 30' including a diffraction grating. The detection apparatus and the detection method of the present invention may employ a detection chip having a metal film 30' including a diffraction grating, as illustrated in FIG. 6. In this case, it is also possible to couple photons and surface plasmon, thereby emitting plasmon scattered light γ from metal film 30'. In this case, prism 20 is not needed. Light irradiation section 110 is disposed on the side of metal film 30' of the detection chip, and irradiates the diffraction grating with excitation light α in the detection step of fluorescence β as well as the detection step of plasmon scattered light γ.

In the above embodiment, detection operations of the SPFS apparatus including steps of setting an incident angle to an enhanced angle (step S320), stirring (step S330), performing a primary reaction (step S340), and measuring an optical blank value (step S350) in this order are described. The detection method and the detection apparatus of the present invention are not limited to such a sequence. An incident angle may be set to an enhanced angle after performing a primary reaction, or a primary reaction may be performed after measuring an optical blank value.

In the above embodiment, the detection step of the analyte contained in the specimen performed by a SPFS method is described. The detection method and the detection apparatus of the present invention are not limited to this. The detection step may be performed by an enzyme-linked immunosorbent assay (ELISA), reflectometric interference spectroscopy (RIfS), a surface plasmon resonance (SPR) method, or a quartz crystal microbalance (QCM) method, for example.

EXAMPLES

Hereinafter, the present invention will be described more specifically with reference to the Examples, but the present invention is never limited to the Examples below.

Example 1

(1) Measurement of Hematocrit

A whole blood sample with a hematocrit of 40% (500 μL) was fed into a container and left standing for 30 minutes to precipitate blood cells. The container that held the sample with precipitated blood cells was set in the SPFS apparatus of the embodiment. The sample inside the container (200 μL) was drawn in a state after the leading end of the pipette tip was moved to a position at 1/7 the height of the container from the container bottom surface (in a region where blood cells were precipitated), and the drawn sample (200 μL) was discharged in a state after the leading end of the pipette tip was moved to 2 mm above the liquid surface of the sample. The discharge rate of the sample was set to 10,000 μL/min. These stirring operations were performed five times. After the stirring, the sample (100 μL) inside the container was collected at the position of 1/7 the height of the container from the container bottom surface, and the hematocrit was measured by a microhematocrit method. The hematocrit was 42%, and thus no major discrepancy was observed between the measured value and the original hematocrit (40%).

(2) Detection of Analyte (Preparation of Detection Chip)

A detection chip, in which anti-troponin I antibody (anti-cTnI antibody) is immobilized as a capturing body in a reaction site above a metal film, was prepared. The prepared detection chip was loaded on a chip holder of the above-mentioned SPFS apparatus.

(Stirring/Detection of Whole Blood Sample)

1) A whole blood sample (500 μL) with a hematocrit of 40% containing troponin I (cTnI) as an antigen was fed into a container. The container that held the sample was set in the SPFS apparatus, and stirring was performed substantially the same conditions as those described in (1). The sample (100 μL) was collected at the position of 1/7 the height of the container from the container bottom surface (in a region where blood cells were precipitated), supplied to a channel of the detection chip, and assayed by a sandwich immunoassay. Signal value S1 was thus obtained.

2) A whole blood sample (500 μL) same as that of 1) was fed into a container. Immediately, the sample (100 μL) was collected at the position of 1/7 the height of the container from the container bottom surface, supplied to the channel of the detection chip, and assayed in substantially the same manner as 1) to obtain signal value S2. Signal value S2 corresponds to a signal value in a state without precipitation of blood cells.

3) A lowering rate of the signal values was calculated by substituting the signal values obtained in 1) and 2) into the following equation.

$$\text{Lowering rate of signal values}(\%) = \{(\text{signal value } S2 - \text{signal value } S1)/\text{signal value } S2\} \times 100$$

The lowering rate of signal values was 2%, and thus found to be nearly unchanged compared to a case without precipitation of blood cells.

Comparative Example 1

(1) Measurement of Hematocrit

The hematocrit was measured in substantially the same manner as Example 1, except for performing no stirring of the sample inside the container. The hematocrit was 62%, and a large discrepancy was observed between the measured value and the original hematocrit (40%).

(2) Detection of Analyte

The assay was performed in substantially the same manner as Example 1 except for performing no stirring of the sample inside the container. The lowering rate of signal values was about 30%, and thus a large lowering rate of signal values was observed compared to that in a state without precipitation of blood cells.

Comparative Example 2

(1) Measurement of Hematocrit

The hematocrit was measured in substantially the same manner as Example 1 except for performing, five times, stirring operations in which a sample (200 μL) inside the container was drawn, and then the drawn sample was discharged inside the container while the leading end of the pipette tip was fixed at the position of 1/7 the height of the container from the container bottom surface (in a region where blood cells were precipitated). The hematocrit was 60%, and thus found to differ from the original hematocrit (40%) largely.

(2) Detection of Analyte

The sample was assayed in substantially the same manner as Example 1 except for performing, five times, stirring operations in which a sample (200 μL) inside the container was drawn, and then the drawn sample was discharged inside the container while the leading end of the pipette tip was fixed at the position of ½ the height of the container from the container bottom surface (in a region where blood cells were precipitated). The lowering rate of signal values was about 28%, and thus found to be significant lowering in signal values compared to that in a state without precipitation of blood cells.

This application is entitled to and claims the benefit of Japanese Patent Application No. 2015-136022, filed on Jul. 7, 2015, the disclosure of which including the specification and drawings is incorporated herein by reference in its entirety.

REFERENCE SIGNS LIST

10 Detection chip
20 Prism
21 Incident surface
22 Film forming surface
23 Emission surface
30 Metal film
40 Channel lid
41 Channel
100 SPFS apparatus
110 Light irradiation section
111 Light source unit
112 Angle adjustment section
113 Light source control section
120 Light detection section
121 Light-receiving optical system unit
122 Position switching section
123 Sensor control section
124 First lens
125 Optical filter
126 Second lens
127 Light-receiving sensor
130 Liquid feed section
131 Container
132 Pipette
133 Pipette moving section
134 Liquid feed pump driving section
135 Syringe
136 Plunger
137 Pipette nozzle
138 Pipette tip
140 Conveyance section
141 Conveyance stage
142 Chip holder
150 Control section
α Excitation light
β Fluorescence
γ Plasmon scattered light

The invention claimed is:

1. A detection apparatus for detecting an analyte contained in a specimen containing a plurality of substances with different specific gravities, comprising:
a pipette that allows a pipette tip to be detached therefrom, and that draws or discharges a specimen inside a container;
a pipette mover that moves the pipette; and
a controller that controls the pipette and the pipette mover, wherein:
the controller controls the pipette and the pipette mover so as to stir the specimen containing a plurality of substances with different specific gravities by causing the pipette to draw at least part of the specimen inside the container in a state after a leading end of the pipette tip is moved to a position A in a region where a substance with a relatively high specific gravity in the specimen inside the container is concentrated on a lower side of the container by the pipette mover, then the pipette to discharge, at least partially, the drawn specimen to the inside of the container in a state after the leading end of the pipette tip is moved to a position B above the position A above the region where the substance with the relatively high specific gravity in the specimen inside the container is concentrated by the pipette mover, and then the leading end of the pipette tip is moved to the position A in the region where the substance with the relatively high specific gravity in the specimen inside the container is concentrated on the lower side of the container by the pipette mover without discharging the drawn specimen,
wherein the pipette is configured to discharge the drawn specimen with the leading end of the pipette tip being more than 0 mm and 15 mm or less apart from the liquid surface of the specimen inside the container.

2. The detection apparatus according to claim 1, wherein the pipette mover moves the pipette in a vertical direction.

3. The detection apparatus according to claim 1, wherein when the pipette discharges the drawn specimen, the leading end of the pipette tip is located above a liquid surface of the specimen inside the container.

4. The detection apparatus according to claim 3, wherein when the pipette discharges the drawn specimen, the leading end of the pipette tip is positioned so that the drawn specimen is discharged to a central portion of the liquid surface of the specimen inside the container.

5. The detection apparatus according to claim 1, wherein a discharge rate when the pipette discharges the drawn specimen is 1,000 to 15,000 μL/min.

6. The detection apparatus according to claim 1, wherein an amount of the specimen drawn or discharged by the pipette is 20% by volume or more of an amount of the specimen held in the container.

7. The detection apparatus according to claim 1, wherein the controller switches, in accordance with a type or an amount of the specimen, the number of times the pipette draws and discharges the specimen, and/or positions of the leading end of the pipette tip when the pipette draws or discharges the specimen.

8. The detection apparatus according to claim 1, wherein the specimen contains a plurality of substances with different specific gravities.

9. The detection apparatus according to claim 8, wherein the specimen is blood or diluted blood.

10. The detection apparatus according to claim 8, wherein when the pipette draws the specimen inside the container, the leading end of the pipette tip is located in a region where a substance with a relatively high specific gravity in the specimen inside the container is concentrated.

11. A detection method comprising:
stirring a specimen containing a plurality of substances with different specific gravities inside a container by drawing at least part of the specimen inside the container by a pipette in a state after a leading end of a pipette tip fixed to the pipette is moved to a position A in a region where a substance with a relatively high specific gravity in the specimen inside the container is concentrated on a lower side of the container, discharging, at least partially, the drawn specimen by the pipette in a state after the leading end of the pipette tip is moved to a position B above the position A above the region where the substance with the relatively high specific gravity in the specimen inside the container is concentrated, and then moving the leading end of the pipette tip to the position A in the region where the substance with the relatively high specific gravity in the specimen inside the container is concentrated on the lower side of the container by the pipette mover without discharging the drawn specimen; and detecting an analyte contained in the stirred specimen, wherein the pipette discharges the drawn specimen with the leading end of the pipette tip being more than 0 mm and 15 mm or less apart from the liquid surface of the specimen inside the container.

12. The detection method according to claim 11, wherein when the pipette discharges the drawn specimen during the stirring, the leading end of the pipette tip is located above a liquid surface of the specimen inside the container.

13. The detection method according to claim 11, wherein a discharge rate when the pipette discharges the drawn specimen during the stirring is 1,000 to 15,000 µL/min.

14. The detection method according to claim 11, wherein the specimen is blood or diluted blood.

15. The detection method according to claim 11, wherein when the pipette draws the specimen inside the container during the stirring, the leading end of the pipette tip is located in a region where a substance with a relatively high specific gravity in the specimen inside the container is concentrated.

16. The detection method according to claim 11, wherein detection is performed by surface plasmon-field enhanced fluorescence spectroscopy (SPFS) during the detecting.

* * * * *